(12) United States Patent
Guo

(10) Patent No.: US 9,764,305 B2
(45) Date of Patent: Sep. 19, 2017

(54) GEOMETRY ENHANCEMENT OF NANOSCALE ENERGY DEPOSITION BY X-RAYS

(71) Applicant: The Regents of the University of California, Oakland, CA (US)

(72) Inventor: Ting Guo, Davis, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 145 days.

(21) Appl. No.: 14/391,003

(22) PCT Filed: Mar. 15, 2013

(86) PCT No.: PCT/US2013/032604
§ 371 (c)(1),
(2) Date: Oct. 6, 2014

(87) PCT Pub. No.: WO2013/151772
PCT Pub. Date: Oct. 10, 2013

(65) Prior Publication Data
US 2015/0083579 A1    Mar. 26, 2015

Related U.S. Application Data

(60) Provisional application No. 61/621,386, filed on Apr. 6, 2012.

(51) Int. Cl.
*B01J 19/12* (2006.01)
*C09B 11/24* (2006.01)
(Continued)

(52) U.S. Cl.
CPC ......... *B01J 19/125* (2013.01); *A61K 41/0028* (2013.01); *B01J 13/22* (2013.01);
(Continued)

(58) Field of Classification Search
CPC .. B01J 19/125; B01J 13/22; B01J 2219/1203; C09B 11/24; C09B 67/0097; A61K 41/0028
(Continued)

(56) References Cited

U.S. PATENT DOCUMENTS 6,428,811 B1* 8/2002 West ............... A61K 41/0028
424/497
7,538,329 B2* 5/2009 Chen ................... A61B 5/0059
250/370.07
(Continued)

OTHER PUBLICATIONS

International Application No. PCT/US2013/032604, "International Search Report and Written Opinion," mailed Jun. 10, 2013, 6 pages.

*Primary Examiner* — Keith Hendricks
*Assistant Examiner* — Colleen M Raphael
(74) *Attorney, Agent, or Firm* — Kilpatrick Townsend & Stockton LLP

(57) ABSTRACT

A principle is established to show that nanoscale energy deposition in water by X-rays can be greatly enhanced via the geometry of nanostructures. The calculated results show that enhancement over background water can reach over 60 times for a single nanoshell made of gold. Other geometries and nanostructures are investigated, and it is found that a shell of gold nanoparticles can generate similar enhancement. The concepts of composition, matrix, and satellite effects are established and studied, all of which can further increase the enhancement of the effect of X-rays.

26 Claims, 16 Drawing Sheets

(51) Int. Cl.
  *B01J 13/22* (2006.01)
  *A61K 41/00* (2006.01)
  *C09B 67/02* (2006.01)

(52) U.S. Cl.
  CPC .......... *C09B 11/24* (2013.01); *C09B 67/0097* (2013.01); *B01J 2219/1203* (2013.01)

(58) Field of Classification Search
  USPC .................................................. 204/157.44
  See application file for complete search history.

(56) References Cited

U.S. PATENT DOCUMENTS

| | | | |
|---|---|---|---|
| 8,033,977 B2* | 10/2011 | Hainfeld | A61K 49/222 |
| | | | 600/1 |
| 8,075,664 B1 | 12/2011 | Wang et al. | |
| 9,211,419 B2* | 12/2015 | Krishnan | A61N 2/002 |
| 9,302,003 B2* | 4/2016 | Sanche | A61K 9/0019 |
| 2001/0002275 A1 | 5/2001 | Oldenburg et al. | |
| 2002/0103517 A1 | 8/2002 | West et al. | |
| 2005/0079131 A1* | 4/2005 | Lanza | A61K 49/049 |
| | | | 424/1.11 |
| 2008/0003183 A1* | 1/2008 | Guo | A61K 41/0038 |
| | | | 424/9.42 |
| 2008/0169753 A1* | 7/2008 | Skipor | B41M 3/006 |
| | | | 313/504 |
| 2009/0294692 A1 | 12/2009 | Bourke et al. | |
| 2010/0003316 A1* | 1/2010 | Vo Dinh | A61K 41/0028 |
| | | | 514/1.1 |
| 2010/0016783 A1* | 1/2010 | Bourke, Jr. | A61K 41/0057 |
| | | | 604/20 |
| 2010/0040549 A1* | 2/2010 | Halas | A61K 41/0028 |
| | | | 424/9.1 |
| 2011/0021970 A1 | 1/2011 | Vo Dinh et al. | |
| 2011/0318415 A1 | 12/2011 | Li et al. | |
| 2012/0083761 A1* | 4/2012 | Malecki | A61K 41/0038 |
| | | | 604/500 |
| 2012/0145532 A1* | 6/2012 | Smolyakov | B01J 21/063 |
| | | | 204/157.44 |
| 2015/0265725 A1* | 9/2015 | Peyman | A61K 49/227 |
| | | | 600/2 |

* cited by examiner

Figure 7

| Shape | | | | | | |
|---|---|---|---|---|---|---|
| Enh | 7.4 | 9.2 | 12.4 | 18.5 | 4.8 | 4.1 |
| Params | radius VOI = 40<br>radius Ball = 17<br>X-ray = 40 | radius VOI = 40<br>radius Ball = 15<br>X-ray = 40 | radius VOI = 40<br>radius Ball = 12<br>X-ray = 40 | radius VOI = 40<br>thickness = 10<br>X-ray = 40 | Plate length = 50<br>Gap = 10<br>thickness = 1<br>X-ray = 83 | Plate length = 50<br>Gap = 10<br>radius Ball = 3<br>X-ray = 83 |

Figure 14

| | | Processes | Program Packages/Database |
|---|---|---|---|
| e⁻ emission | | • Ionization<br>• Auger Cascade | Geant4 Low Energy Electromagnetic Package<br>• G4CrossSectionHandler (EPDL97)<br>• G4AtomicDeexcitation (EADL) |
| e⁻ transport | $H_2O$ | Event-by-Event Simulation | NOREC |
| | Au and others | Elastic Scattering | NIST Electron Elastic-Scattering Cross-Section Database |
| | | Mean Free Path | NIST Electron Inelastic Mean Free Path Database |
| | | Continuous Energy Loss | Bethe Stopping Power (Joy, Luo) |

GEOMETRY ENHANCEMENT OF NANOSCALE ENERGY DEPOSITION BY X-RAYS

CROSS REFERENCE TO RELATED APPLICATIONS

This is a U.S. National Phase patent application of PCT/US2013/032604, filed Mar. 15, 2013, which claims the benefit of U.S. Provisional Application No. 61/621,386, filed Apr. 6, 2012, each of which is hereby incorporated by reference in the present disclosure in its entirety.

STATEMENT REGARDING FEDERALLY-SPONSORED RESEARCH

This invention was made with Government support under Grant No. CHE0957413 awarded by the National Science Foundation. The Government has certain rights in this invention.

FIELD

The present disclosure relates to the field of nanomaterial compositions, and more specifically to the field of enhancement of ionizing radiation energy deposition by nanomaterial compositions.

BACKGROUND

X-ray absorption by materials plays an important role in a large number of applications ranging from therapy to detection to imaging. Upon absorption of X-rays, energy is released from the absorbing material and deposited in the surrounding material, which is then converted to chemical or other forms of energy. It is possible to expand the application potential of X-rays by manipulating the host materials to control the absorption of X-rays and geometry of energy deposition. Therefore, investigating the mechanism of X-ray absorption and energy deposition is essential to finding the optimal nanostructures that can create maximal nanoscale (1 to a few hundred nanometers) energy deposition from the absorption of hard X-ray radiation.

Such energy deposition can be studied by following the events experienced by the electrons and photons released from materials as the result of absorption of primary X-ray photons. In most cases the majority of energy released from the absorbing material is carried away in photoelectrons. The released photoelectrons (and in a few cases Auger electrons) are often energetic enough (>5 keV in kinetic energy) to travel micrometers to tens of micrometers in the surrounding media such as water. We call this the remote effect or Type 1 Physical Enhancement (T1PE) because this dimension is much greater than the nanoscale dimensions mentioned above. Most of the recent reports of employing nanomaterials to enhance the effect of X-rays have cited this mechanism as the basis for designing their experiments and interpreting their results.[1-3] A general rule of thumb is that adding one weight percent (1 wt %) of gold nanomaterials dissolved in water may generate up to 140% T1PE compared with background water. Such an enhancement can cause a similar amount of increase in the production of reactive oxygen species (ROS) such as hydroxyl radicals (.OH), as long as there are no other side effects such as scavenging of radicals by the introduced nanomaterials. However, contrary to what is commonly believed by researchers working in this field, this mechanism may not play a major role in many applications because it is difficult to dissolve 1 wt % of gold nanoparticles into water without introducing significant amounts of scavengers.

In addition to the energetic photoelectrons, there are low-energy (<5 keV) photoelectrons, Auger and secondary electrons generated upon absorption of X-rays. These electrons, although carrying only a fraction of the total energy released to the surrounding, can generate greater densities of energy deposition around the absorbing materials due to the much shorter distances (a few to a few hundred nanometers) traveled by these low-energy electrons in water. Because the penetration depth of these electrons in water is of the order of nanometers, it is possible to achieve higher energy deposition densities if the geometry and/or composite of nanomaterials are so arranged as to increase the overlap of trajectories of these low-energy electrons. This type of energy deposition is referred to as nanoscale energy deposition or Type 2 Physical Enhancement (T2PE), and this concept is the basis for geometry enhanced nanoscale energy deposition. In addition to giving rise to geometry enhancement, using nanomaterials has several other advantages. First, due to the high density of atoms in nanomaterials, they can be much more absorbing to X-rays than molecular complexes within a volume of nanometer dimension. Second, nanomaterials have large surface-to-volume ratios, which favor the escape of low-energy electrons, making them much more preferred than micrometer sized or bulk materials; the latter two can significantly attenuate the low-energy electrons. Third, it is possible to synthesize and assemble nanostructures to maximize energy deposition, thus making geometry enhancement more attainable practically.

To date no reports exist in the area of using nanostructures to maximize nanoscale energy deposition from the absorbed X-rays. Nonetheless, a few studies have dealt with geometry-insensitive enhancement of the effect of X-rays.[4-8] In those studies, various chemical or biological methods such as DNA strand breaks[1, 4, 9], cell and tissue damage[2], and production of fluorescent molecules[10] have been used to probe the enhancement of X-ray radiation in bulk media or near the surface of nanoparticles. One such study discussed nanoscale energy deposition or T2PE due to X-ray absorbing spherical gold nanoparticles.[4] Although no complex geometries were used in that study, the results implied that it is possible to achieve high local T2PE using small amounts of nanomaterials (much less than 1 wt %).

We present here the results of studying how the geometry of nanostructures affects energy deposition and how nanostructures can be used to manipulate energy deposition on the nanometer scale. Such energy deposition may lead to increased amounts of chemical and biological reactions in water.

BRIEF SUMMARY

In one aspect, the present disclosure relates to a method of enhancing deposition of ionizing radiation energy in a solution, the method comprising: a) providing a nanoshell comprising metal atoms, and b) subjecting the nanoshell to ionizing radiation, wherein electrons are released from the metal atoms of the nanoshell and deposition of energy from the ionizing radiation is enhanced in the solution adjacent to the nanoshell. In some embodiments, the metal atoms are from a heavy metal. In some embodiments, the heavy metal is selected from the group consisting of gold, platinum, bismuth, uranium, and tungsten. In some embodiments, the metal atoms are selected from the group consisting of iron, zinc, and silver. In some embodiments, the nanoshell further comprises at least one of silicon and oxygen. In some embodiments, the nanoshell is continuous. In some embodiments, the nanoshell comprises a shell of nanoparticles. In some embodiments, the shell of nanoparticles comprises gold nanoparticles. In some embodiments, the nanoshell further comprises a lipid. In some embodiments, the ionizing radiation is X-rays. In some embodiments, the enhancement is a 60-fold increase in the deposition of energy from the ionizing radiation in the solution adjacent to the nanoshell when compared to the deposition of energy from the ionizing radiation in the background solution.

In a further aspect, the present disclosure relates to a method of enhancing deposition of ionizing radiation energy in a solution, the method comprising: a) contacting a nanoshell comprising metal atoms with ionizing radiation, and b) releasing electrons from the metal atoms of the nanoshell, wherein deposition of energy from the ionizing radiation is enhanced in the solution adjacent to the nanoshell. In some embodiments, the metal atoms are from a heavy metal. In some embodiments, the heavy metal is selected from the group consisting of gold, platinum, bismuth, uranium, and tungsten. In some embodiments, the metal atoms are selected from the group consisting of iron, zinc, and silver. In some embodiments, the nanoshell further comprises at least one of silicon and oxygen. In some embodiments, the nanoshell is continuous. In some embodiments, the nanoshell comprises a shell of nanoparticles. In some embodiments, the shell of nanoparticles comprises gold nanoparticles. In some embodiments, the nanoshell further comprises a lipid. In some embodiments, the ionizing radiation is X-rays. In some embodiments, the enhancement is a 60-fold increase in the deposition of energy from the ionizing radiation in the solution adjacent to the nanoshell when compared to the deposition of energy from the ionizing radiation in the background solution.

DESCRIPTION OF THE DRAWINGS

FIG. 7 illustrates practical cases. Nanoparticle-decorated nanoshells, a true nanoshell, a dual-plate, and two stacks of nanoparticles are studied here. The nanoparticle-decorated nanoshell and dual-plate may be more easily synthesized and utilized in practice. (dimension units: nm; X-ray energy unit: keV)

FIG. 11A and FIG. 11B show the contour plots of nanoshells and nanoeggs. The yolk of the nanoeggs is kept at 25 nm radius. The energy of X-rays is 81 keV. The thickness of the nanoshell and the shell in nanoeggs is varied. FIG. 11C and FIG. 11D show the enhancement of two nanoshells (FIG. 11C) and two nanoeggs (FIG. 11D).

FIG. 12A shows the total mass effect on nanoeggs and FIG. 12B shows that of each layer in a nano shell. X-ray energy is fixed at 40 keV. Each mass unit has $10^5$ nm$^3$ gold, and 4, 8, 16, and 32 units are used in the study. Both results show that more mass results in greater enhancement. FIG. 12B further shows that mass from different layers in a nanoshell contributes to the enhancement differently. The most inner layer is the most effective layer.

FIG. 14 illustrates the parameters used in this simulation. All the physical parameters are available in the literature and no new measurements were performed in this calculation to improve those parameters. These parameters are used in the simulation as described in FIG. 2 and FIG. 8.

FIG. 15A illustrates a proposed mechanism of cargo release from the liposomes coated with gold nanoparticles following X-ray irradiation. FIG. 15B illustrates a cryo transmission electron microscope image of liposomes without gold nanoparticles. Scale bar denotes a length of 500 nanometers (nm). FIG. 15C illustrates the release of the content inside the liposomes upon breaking the liposomes with UV radiation (254 nm) assayed in terms of normalized percent (%) release. FIG. 15D illustrates dynamic light scattering data from three samples: the gold nanoparticles, the DPPE/DPPC liposomes, and a mixture of the two.

FIG. 16A is a graphical depiction of formation of a polymersome by mixing amphiphillic nanoparticles in water. FIG. 16B illustrates the polymersomes formed from 15-nm gold nanoparticles coated with the amphiphillic ligands of polyethylene glycol (PEG) and poly methyl methacrylate and vinylpyridine (PMMAVP). Scale bar denotes a length of 100 nanometers (nm). FIG. 16C illustrates the release of sulforhodamine B (SRB) dye molecules from polymersomes in response to pH adjustment. FIG. 16D illustrates the enhanced destruction of SRB inside the polymersomes caused by X-ray irradiation of the polymersomes.

DETAILED DESCRIPTION

Figure 1:
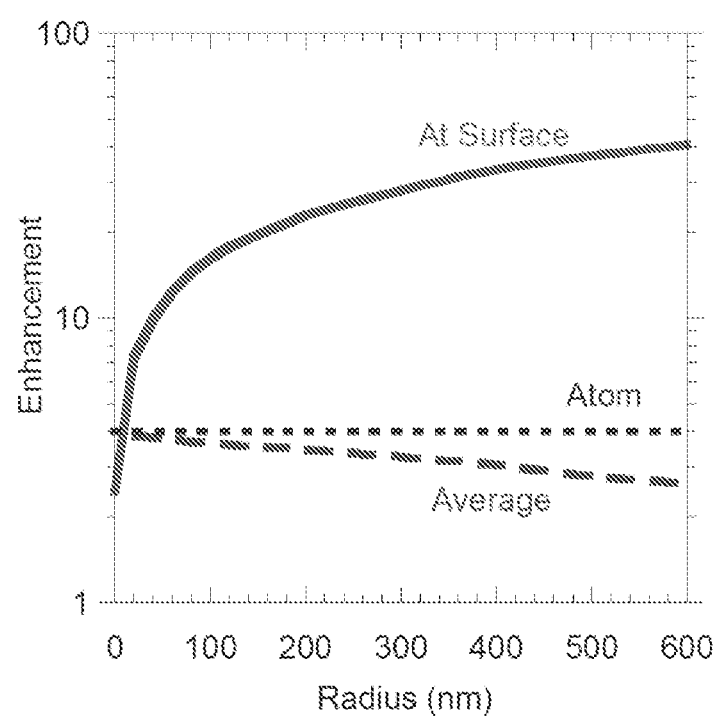
FIG. 1 illustrates a comparison of energy deposition profiles of atoms and spherical nanoparticles. The average energy deposition in bulk water by the introduced materials (dashed line) and that at the surface (5-nm layer within the surface, solid line) are shown. Gold atoms (2 wt %) are chosen to give an overall 4× enhancement of energy deposition (dotted line) over the background water. The total weight of gold is maintained the same for atoms and nanoparticles. The results are calculated at 40 keV X-ray energy.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims. References cited are incorporated herein by reference.

The present disclosure relates to the field of nanomaterial compositions, and more specifically to the field of enhancement of ionizing radiation energy deposition by nanomaterial compositions.

In particular, the present disclosure is based, at least in part, on the development of specially arranged nanostructures that may create enhancement of energy deposition from X-ray absorption by these nanostructures. The coating of gold nanoparticles around liposomes may improve triggered release of molecules stored in the liposomes. Further, gold nanoparticle-containing polymersomes may be used to improve triggered release of molecules in the polymersome. Thus, the present disclosure demonstrates an exemplary manner to construct nano structures that may allow for geometry enhancement of energy deposition when these nanostructures are irradiated with X-rays in water or other media.

Nanoshells

A nanoshell for enhancing energy deposition by X-rays, wherein the nanoshell comprises metal atoms or metal oxides and has a ratio of nanoshell radius to nanoshell thickness between 1:50 and 50:1 is provided herein. In one format, the ratio of nanoshell radius to nanoshell thickness is about 17:40. In some embodiments, the radius of the nanoshell is between 10 nm and 200 nm, and the thickness of the nanoshell is between 1 nm and 100 nm.

The nanoshell for enhancing energy deposition by X-rays may be of various structures. In one aspect, at least 95% of the atoms in the nanoshell are metal atoms. In one aspect, the nanoshell is solid metal. In another aspect, the nanoshell includes scaffolding molecules and nanoparticles on the scaffolding molecules, where the metal atoms are in the nanoparticles. Scaffolding molecules for supporting nanoparticles in the nanoshell include, without limitation, lipid bilayers, micelles, dendrimer nanoparticles, carbon nanoparticles, and polymer nanoparticles such as those made of peptides, proteins, DNA, and biomolecules. In some aspects, the radius of the lipid bilayer or other nanoparticles is between 10 nm and 100 nm. The size of nanoparticles can range from 5 nm to 500 nm, and commonly may be between 10 and 100 nm. The spacing between the nanoparticles may between 1 nm and 500 nm, and ideally 10% to 90% of the diameter of the nanoparticles. The distance between the nanoparticles and the inner may vary from 1 nm to 100 nm, and ideally the distance is between 1 and 50 nm. The nanoparticles can be covalently or electrostatically linked to the surface of the inner shell scaffolding molecules, which can, for example, be a spherical nanoparticle made of liposomes, micelles, dendrimers, and polymers.

Various metal atoms are known in the art and may be used in the nanoshells of the present disclosure. For example, nanoshells may include metal atoms from heavy metals such as gold, platinum, bismuth, uranium, tungsten, other rare earth metals, or any combination thereof. Nanoshells may also include, for example, other elements such as silicon, oxygen, iron, zinc and silver.

Metal atoms in the nanoshell may be in oxide form. In one format, at least 30% of the metal atoms in a nanoshell are in oxides. The oxides can be rare earth oxides, tungsten oxide or other heavy element oxide.

There may be more than one type of metal atom in the nanoshell. In one example, the nanoshell contains gold atoms.

A method of exposing a target region to electrons is provided herein, the method including the steps of: A) providing a nanoshell as described above; and B) subjecting the nanoshell to X-rays and other forms of ionizing radiation such as electrons, gamma rays, and alpha particles, thereby exposing the target region to electrons released from the metal atoms of the nanoshell.

Nanoshells provided herein may be subjected to varying amount of X-ray energy, for example, from 10 to 1000 keV. In some aspects, nanoshells are exposed to between 80.8 and 95 keV energy, or from between 80.8 and 86 keV.

Commonly, energy deposition is enhanced in the region enclosed by the nanoshell. In some aspects, energy deposition is enhanced in the center of a nanoshells disclosed herein. In some embodiments, the deposition of energy from the ionizing radiation in the solution adjacent to the nanoshell is enhanced when compared to the deposition of energy from the ionizing radiation in the background solution. The enhancement in the deposition may include an increase in the deposition of energy that is, for example, a 2-fold increase, a 4-fold increase, a 6-fold increase, an 8-fold increase, a 10-fold increase, a 15-fold increase, a 20-fold increase, a 30-fold increase, a 40-fold increase, a 50-fold increase, a 60-fold increase, a 70-fold increase, an 80-fold increase, a 90-fold increase, a 100-fold increase, a 120-fold increase, or a 150-fold or more increase in the deposition of energy from the ionizing radiation when compared to the deposition of energy from the ionizing radiation in the background solution.

The methods of the present disclosure may allow for the enhancement of the deposition of energy from ionizing radiation in the solution adjacent to a nanoshell. The deposition of energy from ionizing radiation in the solution adjacent to the nanoshell may occur at a distance of, for example, at least 5 nm, at least 10 nm, at least 15 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, at least 100 nm, at least 110 nm, at least 120 nm, at least 130 nm, at least 140 nm, or at least 150 nm or more adjacent to the nanoshell.

A nanoshell may be continuous or a nanoshell may be a shell of nanoparticles. Continuous nanoshells may include one or more homogenous or heterogeneous metal atoms. A nanoshell including a shell of nanoparticles may include one or more homogenous or heterogeneous metal atoms, or one or more homogenous or heterogeneous nanoparticles.

In some embodiments, nanoshells may contain one or more molecules of interest. The molecules of interest may be water or other solvents or solution. In other formats, the molecules of interest may be nanomaterials or molecules such as high density of nitrobenzene or molecules that can undergo radical chain reactions to cause explosions or polymerization reactions. In other formats, the molecules of interest are chemicals that can be oxidized or reduced by electrons directly such as monomers. In some aspects, the molecules of interest are optical fluorophores. In some aspects, the molecules of interest are cancer probes.

In some embodiments, the nanoshell includes scaffolding molecules and nanoparticles on the scaffolding molecules, where the metal atoms are in the nanoparticles. In some embodiments, the nanoparticles may be gold nanoparticles, where the gold nanoparticles are coated on the surface of a liposome. In some embodiments, a polymersome may contain gold nanoparticles. The lipid molecules in the liposome and/or polymersome may contain polymerizable lipid molecules that polymerize under X-ray irradiation. For example, one such lipid molecule is Bis-Sorb-PC. Upon X-ray irradiation, the lipid molecules may polymerize, create one or more openings in the liposome and/or polymersome, and release any cargos stored inside, such as, for example, molecules of interest. The molecules of interest may be drugs such doxorubicin, sRNAs, peptides, proteins, and other molecules. The conjugation of gold nanoparticles may be achieved with electrostatic interaction between carboxylic ligand (such as, for example, citrate) coated gold nanoparticles and amine terminated lipid molecules (Dipalmitoyl phosphatidyl-ethanolamine, DPPE) mixed with regular lipids (1,2-dipalmitoyl-sn-glycero-3-phosphocholine, DPPC) and Bis-Sorb-PC polymerizable lipids. The ratio of Bis-Sorb-PC to amine terminated lipid to regular lipid molecules may range from 1%:1%:98% to 30%:30%:40%. The liposomes and/or polymersomes may be 50 to 400 nm in diameter, and gold nanoparticles may be 1 to 200 nm in diameter. The coverage of gold nanoparticles on the outer surface of liposomes may be 1 to 80%. For example, a liposome may have 50% coverage with 15 nm gold nanoparticles on 120 nm diameter liposomes.

EXAMPLES

To better facilitate an understanding of the embodiments of the disclosure, the following examples are presented. The following examples are merely illustrative and are not meant to limit any embodiments of the present disclosure in any way.

Example 1: Enhanced Nanoscale Energy Deposition Via Geometry Enhancement

This example demonstrates that nanoscale energy deposition in water by X-rays can be greatly enhanced via the geometry of nanostructures. We have investigated for the first time using X-ray absorbing nanostructures for optimized nanoscale energy deposition. It is found that nanoshells can greatly enhance the energy deposition density on the nanometer scale. The highest enhancement from a single nanoshell with 8 mass units over the background water is approximately 60 times. Other concepts include satellite, matrix, and composition effects are introduced and studied here. Although even higher enhancement may be possible, in practice enhancement between 10 and 50 times may be more readily achievable. This work clearly shows that it is possible to use X-rays to generate localized energy deposition to activate and direct chemical and biological reactions. When combined with other effects such as chemical and biological enhancement, the overall enhancement may be much greater.

Materials and Methods

Modeling Details

We developed a dedicated code to simulate the geometry enhancement from nanostructures under X-ray irradiation. The rate of absorption of monoenergetic X-ray photons of energy γ by a small volume of dv in a nanostructure of gold or other elements of volume V, density ρ, absorption cross-section σ and X-ray photon flux λ can be expressed as $$\lambda \sigma \rho dV \qquad (1)$$

This formula assumes that the attenuation of the X-ray beam is negligible over the size of the nanostructure, and every point in the material experiences the same X-ray flux.

Each photon absorbed generates a number of photoelectrons and Auger electrons (denoted by n(γ)) according to an electron energy distribution P(e|γ), which represents the probability of finding an electron with energy e within de when a photon of energy γ is absorbed. The energy deposition density (defined as EDD) in water per electron is the expected value of energy deposition $\bar{\epsilon}(\vec{r}|e, \vec{r}_0)$ by electrons of initial energies e weighted with probability distribution function $P(e|\gamma)$. $\vec{r}_0$ denotes the position at which electrons are emitted. Hence, the total EDD per photon absorbed at $\vec{r}_0$ is given as $$EDD(\vec{r}|\gamma) = n(\gamma) \int_e de \bar{\epsilon}(\vec{r}|e, \vec{r}_0) P(e|\gamma) \quad (2)$$

For spherical nanoshells or nanoparticles, $\bar{\epsilon}$ and EDD have spherical symmetry and $\vec{r}$ is replaced by r. Multiplication of the two equations (1) and (2) and integration over volume V of the nanostructure give the energy deposition density at a point in water when irradiated with flux $\lambda$, $$EDD_\gamma(\vec{r}|\gamma) = \rho \sigma(\gamma) \lambda(\gamma) n(\gamma) \int_e de P(e|\gamma) \int_V d\vec{r}_0 \bar{\epsilon}(\vec{r}|e, \vec{r}_0) \quad (3)$$

In a matrix notation, if we treat the integral as VE, then the above equation becomes:

$$EDD_\Lambda = \rho VEPN\Sigma\Lambda \quad (4)$$

where N, $\Sigma$ and $\Lambda$ are diagonal matrices with elements given by $n(\gamma)$, $\sigma(\gamma)$ and $\lambda(\gamma)$, respectively. This equation summarizes a series of atomic processes, starting from the absorption of photons ($\Sigma\Lambda$), to the generation of electrons (PN) and then to the energy deposition by these electrons (E).

Both water and nanostructures introduced into water contribute to the total energy deposited in the volume of interest (VOI), which can be a sphere or shell for spherically symmetric nanostructures. The contribution from water is assumed to be uniform over the whole volume, and the enhancement is defined as the ratio of EDD in the VOI from the added nanomaterial plus the surrounding water to just pure water. The definition avoids artificial inflation of enhancement caused by inaccurate calculation of the contribution from background water. To further simplify the calculation, the enhancement is obtained using an adjusted photon flux $\Lambda'$ that yields a unity dose in water $$Enh = \rho(VE)(PN\Sigma\Lambda') = \rho GC. \quad (5)$$

The constant coefficient $\rho$ indicates that the enhancement is proportional to the density of the added material. G (defined via VE) has the geometry information and C (defined via PN$\Sigma\Lambda'$) has the X-ray absorption and electron emission information for the material under investigation. This equation clearly indicates that maximum dose enhancement for a fixed amount of a given material depends on the geometry and composition of nanostructures and X-ray energy.

For a composite nanostructure made of more than one element, the enhancement is given by $$Enh_c = \sum_i \rho_i G_i C_i \quad (6)$$

where $G_i$ is the geometric factor for the ith element computed in the presence of the rest of the materials. The algorithm and parameters used in the simulation are shown in FIG. 8, FIG. 9, and FIG. 14.

Figure 10:
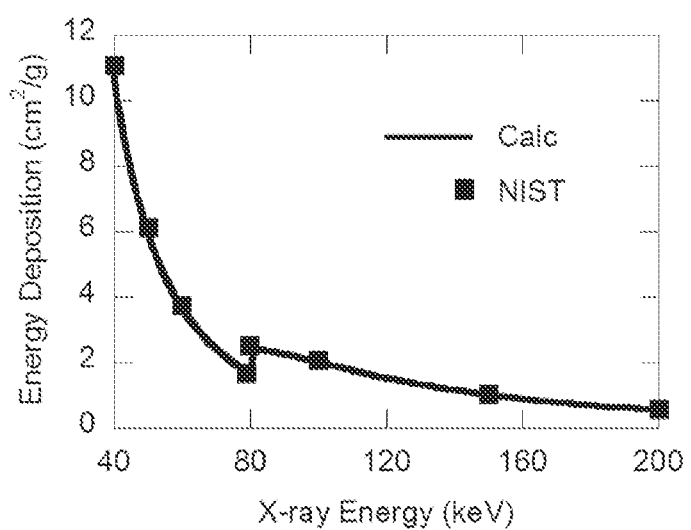
FIG. 10 illustrates the benchmark calculation of the energy deposition in water by electrons generated from gold atoms. The results predicted here (solid line) are in perfect agreement with that of NIST (solid squares), which were calculated at several energies.

A benchmark calculation was performed and the results are shown in FIG. 10. X-rays used in the rest of the manuscript are monochromatic ranging from 40 to 200 keV. Although lower energy X-rays can be better absorbed by gold and water and may alter the outcome, we believe that the X-rays used here represent the range that is commonly accessible by commercially available X-ray sources. Enhancement using various X-ray sources such as X-ray tubes, radioactive elements, and electron accelerators can be conveniently simulated using the results obtained here.

Figure 8:
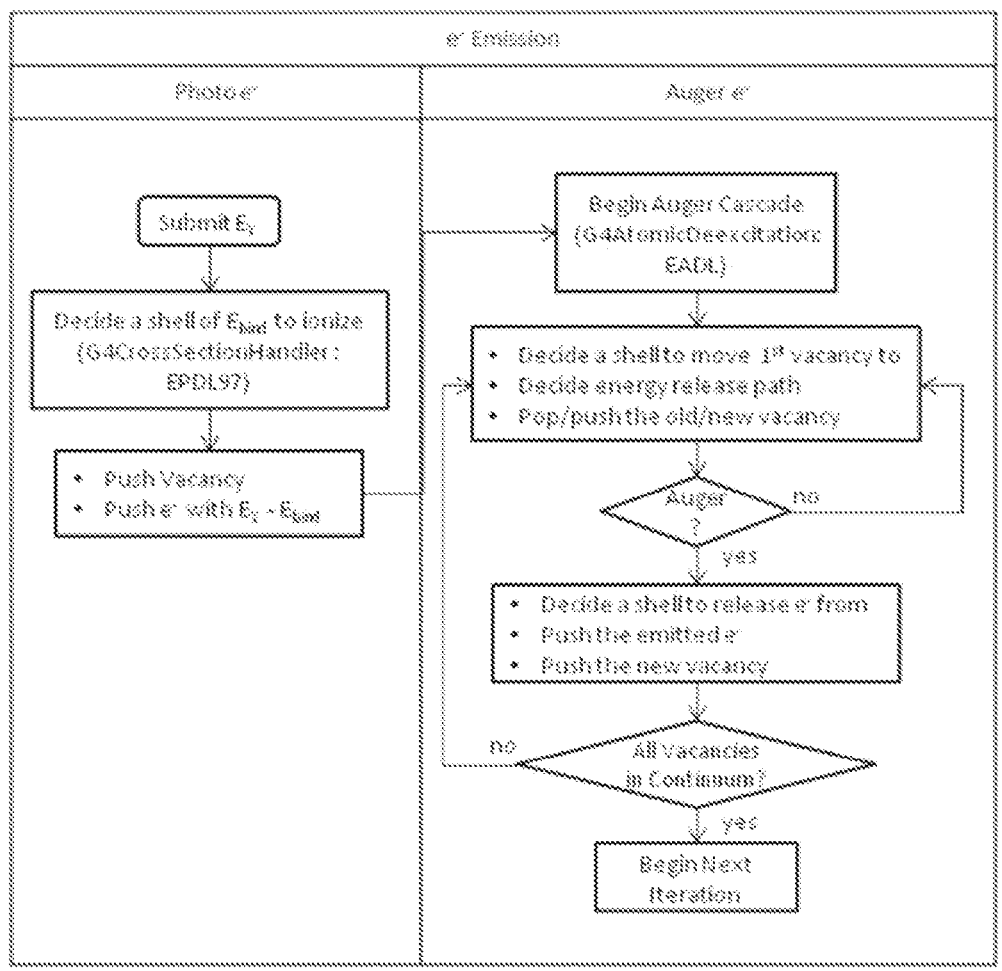
FIG. 8 illustrates a flowchart of the algorithm that tracks the relaxation history of electrons emitted with a distribution of $P(e(\gamma)$ from absorption of an X-ray photon ($E_\gamma$) by an atom. Low Energy Electromagnetic package from Geant 4 Collaboration (G4CrossSectionHandler and G4AtomicDeexcitation) available online is employed in the simulation.[2]
Figure 9:
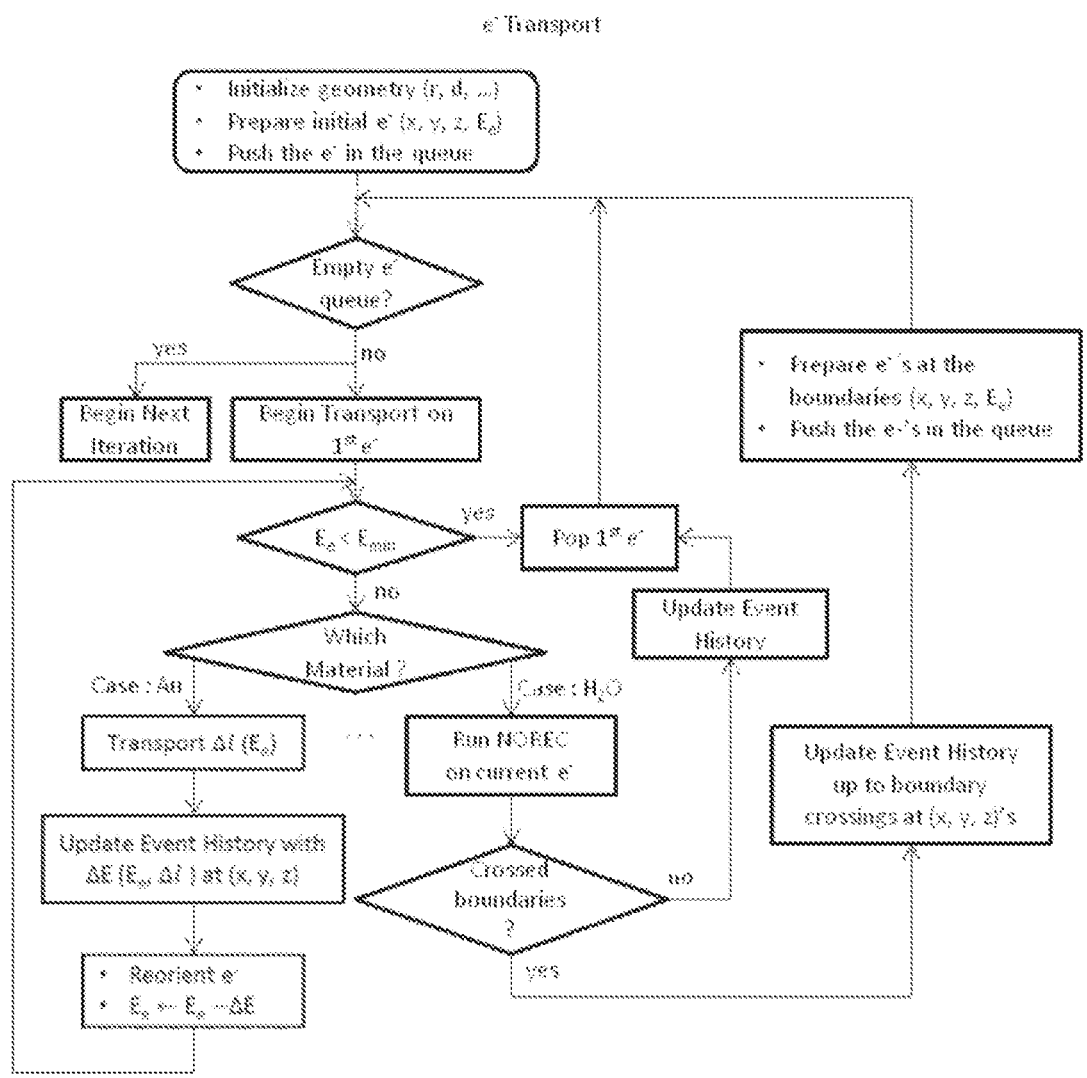
FIG. 9 illustrates a flowchart that shows the routine that is used to perform the electron transport simulation. This routine is repeated with a fixed geometry and at different initial electron energies $E_e$ to obtain the average energy deposition. The initial electron is placed in a chosen starting material (Au, e.g.) at a random position and direction. The electron then enters the electron queue and the transport begins. The NIST electron Inelastic Mean Free Path Database and Electron Elastic-Scattering Cross-Section Database are used in the simulation of transport in Au and the energy lost in each step Δl is computed using a continuous energy loss formula.[3] Once the electron moves out of Au and reaches water, NOREC is used to simulate the transport of both primary and secondary electrons in water.[4] These electrons are tested for boundary crossing and the electrons that enter a material (Au, e.g.) are again placed in the electron queue with the positions $(x_i,y_i,z_i)$ and the energy $E_i$ (i represents the ith electron) at the time of crossing. The electrons are transported individually until the electron queue is empty. Each electron is removed from the queue when the energy goes below $E_{min}$ (7.4 eV) either in water or in other materials.

The algorithm of the simulation performed in this work is described in the flowcharts shown in FIG. 8 and FIG. 9. The main parameters employed in this simulation are given in FIG. 14.

In order to test the validity of this method, a benchmark calculation was performed. The energy transfer coefficient measuring the total energy released in the form of kinetic energy of electrons was studied. Since this parameter describes the atomic processes leading up to X-ray absorption and electron emission but not electron transport and energy deposition in nanomaterials, there is no need to consider the G portion of the formula given in the main article (Eq. (5)). Only the initial energy of electrons at the time of emission was used to set up the calculation. FIG. 10 shows the result. Data points given by the National Institute of Science and Technology (NIST) are also shown for comparison purpose.[1] The agreement between these two is satisfactory.

Results

In the following, we will first discuss the differences between local or nano scale (T2PE) and remote (T1PE) energy deposition, which illustrate the advantages of employing nanostructures. The concepts of composition, satellite, and matrix effects are established and investigated as well. A majority of the results are obtained using gold nanostructures, although nanostructures of several other elements are also investigated.

Advantage of Nanostructures for Geometric Optimization

On the basis of Equation (5) shown above, the energy deposition profile is geometry dependent. For spherical nanoparticles, if only T1PE is considered, which is of average nature, the magnitude of the enhancement over background water is determined by the amount of gold introduced into the system. FIG. 1 shows the results of this T1PE calculation for 2 wt % of gold atoms uniformly distributed in water (blue dotted line) at 40 keV X-ray energy. The enhancement is approximately 400%. The gold atoms are then allowed to aggregate to form spherical nanoparticles of increasingly larger sizes, up to 1200 nm in diameter. Energy deposition in bulk water (dashed line) and that at the surface of nanoparticles (T2PE) (solid line) using a volume of interest (VOI) of 5-nm thick shell right off the surface of the nanoparticles are computed and shown. As the size increases, more energy is retained by the nanoparticles, reducing T1PE from 4.0 to 2.5. In contrast, the enhancement of local energy deposition or T2PE in the VOI increases from 2 to 40 times as the size increases from atoms to 1200 nm diameter, and this enhancement is X-ray energy dependent. The contribution to this local energy deposition enhancement comes mainly from low-energy electrons. The total enhancement is the sum of the two because T2PE is calculated using a single nanoparticle, therefore ignoring nanomaterials in the surrounding. These results suggest that T2PE-based enhancement can be much greater than the remote (bulk) T1PE-based enhancement.

Geometric Optimization

Because energy deposition in water is usually transferred to chemical energy, i.e., more energy deposition gives rise to higher concentrations of hydroxyl radicals (.OH) and other ROS if nanomaterials do not act as ROS scavengers, it is then advantageous to use nanomaterials to increase energy deposition, especially locally and with nanometer precision. Since nanoscale energy deposition or T2PE has a maximum at the surface, it is possible to use nanostructures of various geometries to increase the local energy deposition or T2PE. Several geometries are investigated here.

Spherical Nanoshells

Figure 2:
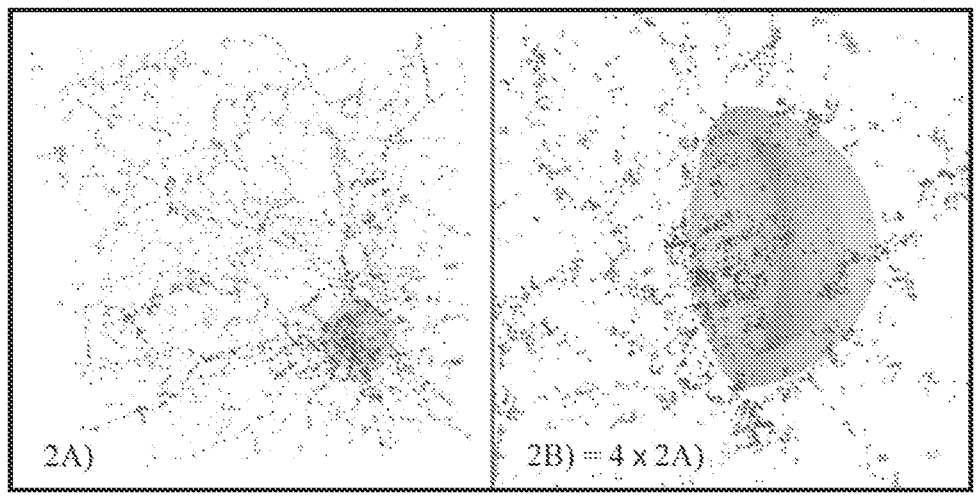
FIG. 2 illustrates energy deposition within and around a spherical nanoshell. The average energy deposition from water and that from the gold are shown in the left panel. The right panel shows a close-up of energy deposition events around the nanoshell. Although there are more events of deposition made outside, the density of energy deposition is much higher inside the nanoshell.

The first geometry we studied is nanoshells. As an example, a nanoshell made of gold with a 100-nm inner ($d_{in}$) and 150-nm outer diameter ($d_{out}$) is used here. The shell is immersed in water. FIG. 2 shows the rationale behind selecting nanoshells. When X-rays are absorbed by such a shell, the density of energy deposition inside the shell (at d<100 nm) can be significantly greater than outside (at d>150 nm). FIG. 2A shows the results of energy deposition events around the nanoshell in water. The tracks represent the events of energy deposition from electrons generated from water and that of the gold nanoshell occurring outside the nanoshell. The tracks representing the events of energy deposition from the gold nanoshell occurring outside the nanoshell densely surround the nanoshell. FIG. 2B shows the spatially magnified tracks near the nanoshell (only a half shell is shown for illustration purposes). Energy deposition events from water electrons are shown as well. Compared with water the gold nanoshell greatly increases the number of absorption and energy deposition events, especially inside the shell.

Figure 3:
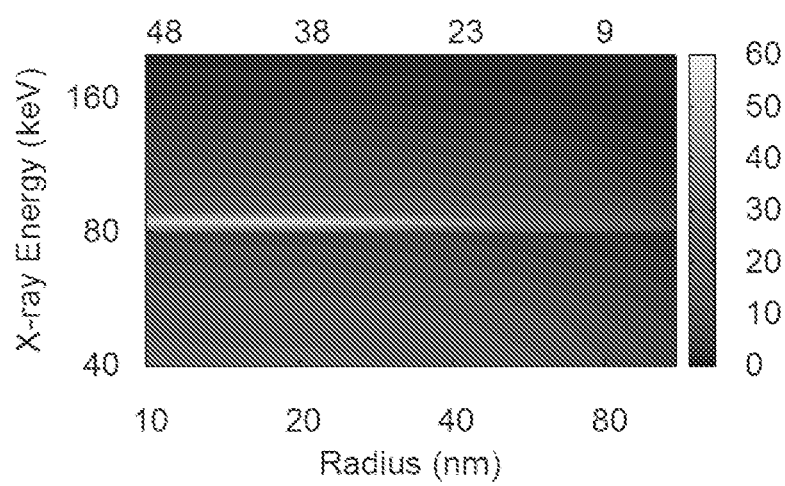
FIG. 3 illustrates nanoshell enhancement. Each nanoshell occupies $8\times10^5$ $nm^3$ or has 8 mass units. The radius and thickness of the nanoshells are varied, as well as X-ray energy. The enhancement as a function of the dimensions and X-ray energy is calculated and shown. The scale is shown with the side bar. Maximum enhancement occurs at 85 keV for a 17-nm radius gold nanoshell.

It is possible to estimate the energy deposition inside different nanoshells. FIG. 3 shows the enhancement pattern of gold nanoshells with a fixed volume or mass but different radii and X-ray energies. The total volume of gold is kept at $8 \times 10^5$ nm$^3$. If we assign the weight of gold in $10^5$ nm$^3$ to a mass unit, then these gold nanoshells all have 8 mass units. As the radius increases, the thickness of the shells decreases to keep the total mass constant. Both radius (lower horizontal axis) and thickness (upper horizontal axis) are displayed in FIG. 3. A maximal 60-time enhancement is achieved with a 17-nm radius and 40-nm thick nanoshell at a few keV above the X-ray absorption edge of Au of 80.7 keV. The enhancement is calculated based on the average enhancement within a VOI of the total internal volume defined by the nanoshells. The manner in which we calculate the enhancement suggests that this predicted 60-time enhancement should be observed experimentally. The highest enhancement is achieved with an optimal combination of X-ray energy and shell radius and thickness. The enhancement is largely attributed to the geometric effect, and is 4 times that of nanoparticles of the same total mass shown in FIG. 1, clearly demonstrating the significance of the geometry enhancement effect.

Spherical Nanoeggs

Figure 11:
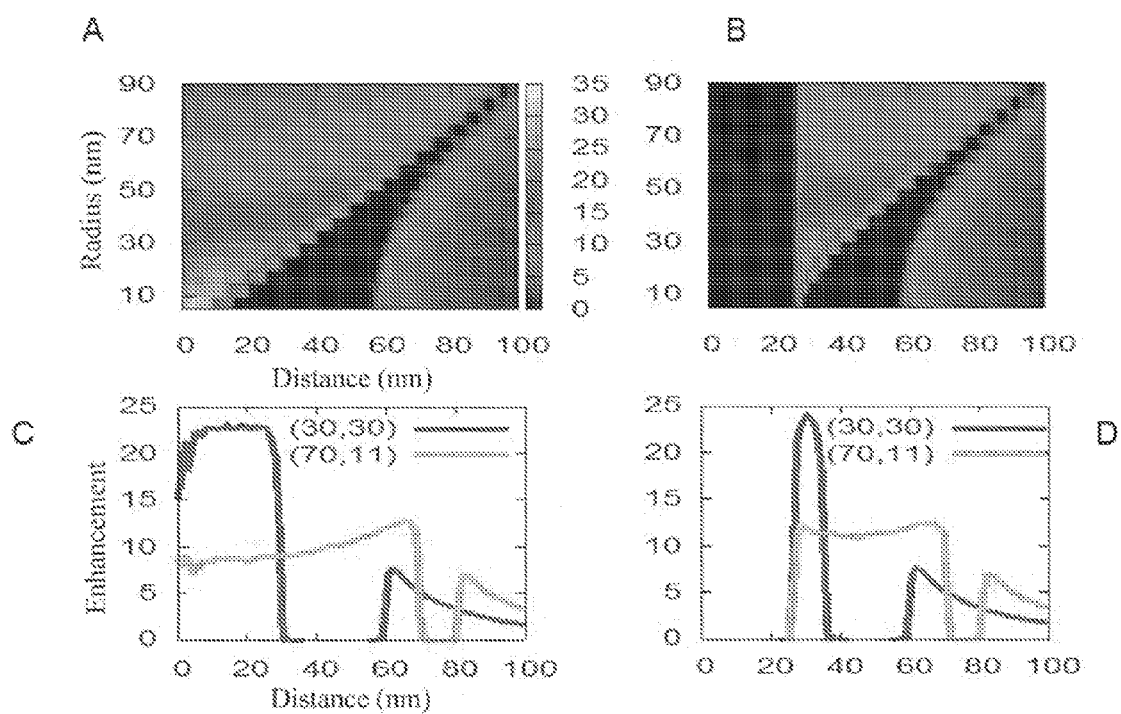
FIG. 11 illustrates geometry enhancement of nanoshells versus nanoeggs.
Figure 12:
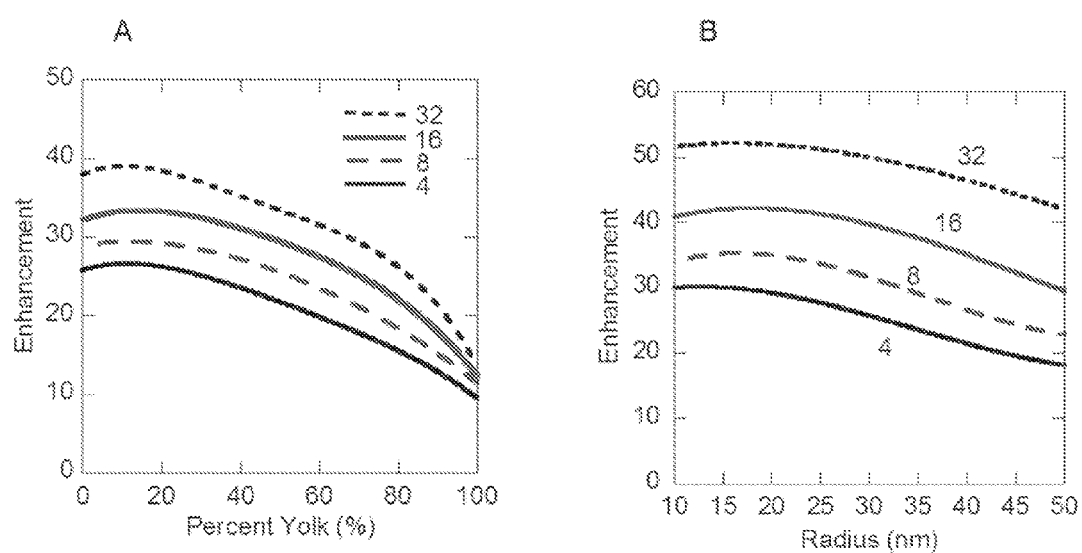
FIG. 12 illustrates the effect of the total mass.

We compared nanoshells with a similar nanostructure, nanoeggs. The yolk, which is a sphere at the center of the shell in nanoeggs, and the shell of nanoeggs are both made of gold. The results are shown in FIG. 11. The highest enhancement occurs near the center for nanoshells and near the yolk for nanoeggs, suggesting that the overlap of electrons going through the inner space leads to the increased enhancement inside. The enhancement was calculated as a function of both the percentage of the mass in the yolk and total mass in nanoeggs. The contribution of different subshells in a nanoshell to the overall enhancement was explored, and the results are shown in FIG. 12. The results show that the innermost layer is the most important. Although addition of each 4-mass unit gold layer to the outside further increases the enhancement, the amount of enhancement decreases from 6.25× per unit mass for a 4-unit mass nanoshell to 1.56× per unit mass for a 32-unit mass shell.

Nanocylinders, Nanotoroids and Nanocages

Figure 4:
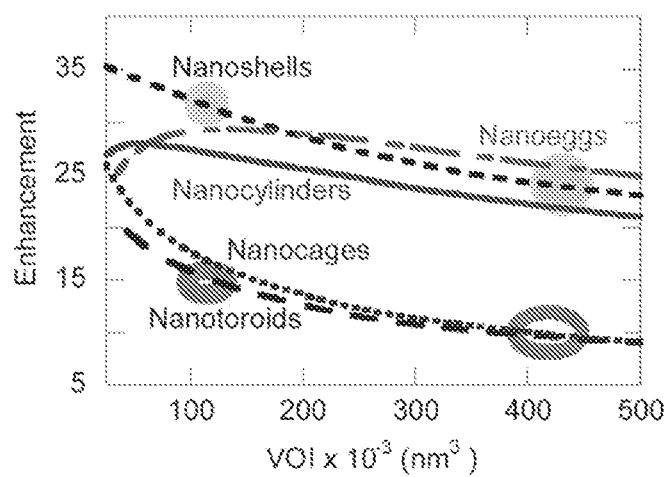
FIG. 4 illustrates shape optimization. Five shapes are calculated: nanoshells (solid line), nanocages (dotted line), nanocylinder (widely spaced dotted line), nanoeggs (dotted dashed line) and nanotoroids (dashed line). The VOIs are defined in the text and it changes as the dimensions of the nanostructures vary. The lines shown here are the results of smoothing of the calculated results, which are obtained with limited number of trajectories.

Other shapes are also explored. FIG. 4 shows the results of nanoshells and four other geometries, including nanocages, nanoeggs, nanocylinders, and nanotoroids, all with equal mass of gold. The X-ray energy is set at 40 keV. The VOI here is the maximum volume of water in the spheres (for nanoshells and nanotoroids), shells (for nanoeggs), cubes (for nanocages), or cylinders (for nanocylinders) that is totally enclosed by these nanostructures. Such a selection of VOI favors nanoshells by the solid angle argument. For nanocylinders, the integrated solid angles for gold covering the VOI are smaller. Nanotoroids are the same—there are materials that are not used efficiently because they are not placed as close to the VOI as possible. From FIG. 4, nanocylinders are similar to nanoshells in generating high enhancements, whereas the enhancement per unit mass of nanotoroids and nanocages is significantly lower. The results again show that nanoshells and nanoeggs are the best geometry to generate the highest enhancement for a fixed amount of gold, which can be understood based on the solid angle facing the VOI subtended by the gold in these nanostructures. However, shapes other than nanoshells may be useful for other purposes.

Composition Optimization

Figure 13:
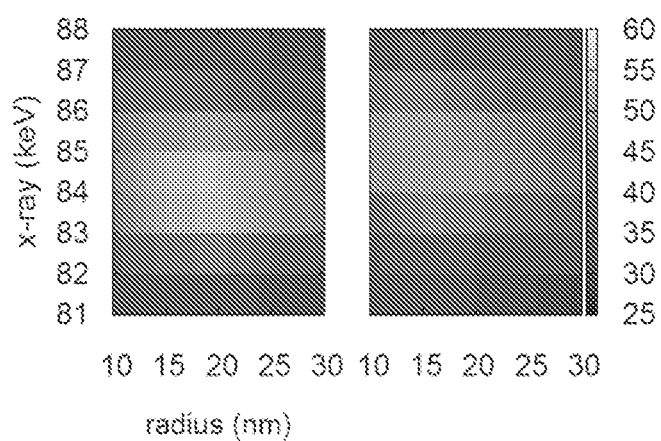
FIG. 13 illustrates composition effect, illustrated by a Pt/Au composite nanoshell, which has 8 mass units with equal amount of Pt and Au. The enhancement increases by about 11% (left panel) when the Pt layer is on the outside. This is because slightly higher kinetic energy is needed for electrons emitted from the outer layer to reach the VOI at the center. For comparison purpose, the right panel shows the all gold case.

With regard to composition, we found that adding a second element to the mix may change enhancement. For example, when Au is partially replaced by Pt in a gold nanoshell, enhancement may increase slightly, depending on the exact geometric configuration and X-ray energy. The results are shown in FIG. 13, which show that adding a second layer of different element may increase the enhancement by 10%.

Satellite Effect

Figure 5:
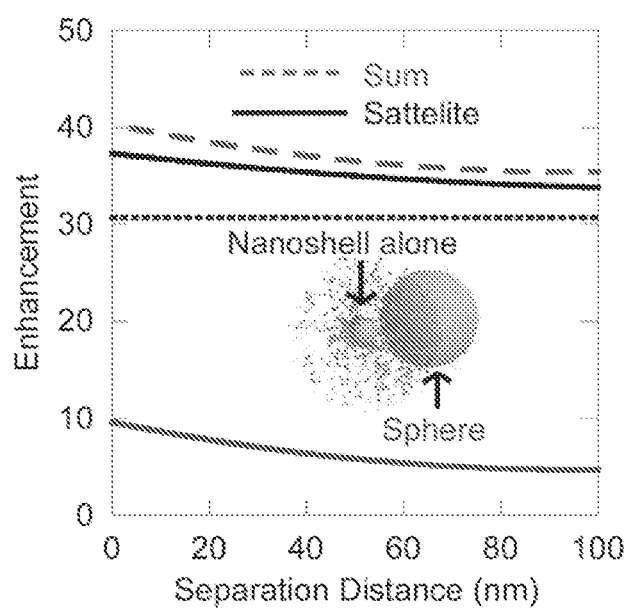
FIG. 5 illustrates satellite effect. A nanoshell (50 nm radius and 30 nm thick) is placed at different distances away from a solid gold nanosphere. X-rays irradiate both. The enhancements are given here. The solid black line shows the total enhancement. The dotted line shows the contribution from the nanoshell alone and the solid line (lower portion of the chart) shows that of the sphere. The dashed line shows the sum of the enhancement from the nanoshell and sphere alone. The satellite enhancement is greater than either the nanoshell or the sphere alone, but is slightly less than the sum of the two, which is due to the net attenuation of the electrons from the sphere by the nanoshell. The calculations were performed for 40 keV X-rays.

When a nanoshell is placed next to a large solid sphere, the enhancement may be greater than either of the nanoshell or sphere alone due to the interaction of the electrons emitted from the sphere with the nanoshell. There may be practical implications for such a geometric arrangement. For example, a number of small nanoshells may be transported into a cell next to a large solid sphere. The outside large nanoparticle can act as a stronger X-ray absorber because of its large mass, and the smaller nanoshells inside the cell can absorb electrons emitted from this large nanoparticle. FIG. 5 shows the enhancement at the center of a nanoshell (50 nm radius and 30 nm thick, and VOI is the total sphere inside the nanoshell) as a function of the distance from a 200-nm radius sphere, both immersed in water. The black solid line shows that total enhancement and the short dashed line shows the enhancement for the nanoshell alone. The enhancement from this arrangement is 5-25% higher than the nanoshells alone, depending on the distance. The X-ray energy used in this calculation is 40 keV. The enhanced portion over the nanoshell is actually slightly less than that contributed from the sphere, due to the net attenuation of electrons coming from the sphere by the nanoshell. It should be noted that this nanoshell is chosen to demonstrate the satellite effect, not the highest enhancement by the nanoshell itself. When the radius of the sphere approaches infinity, this result should resemble a nanoshell next to a wall.

Matrix Effect

Figure 6:
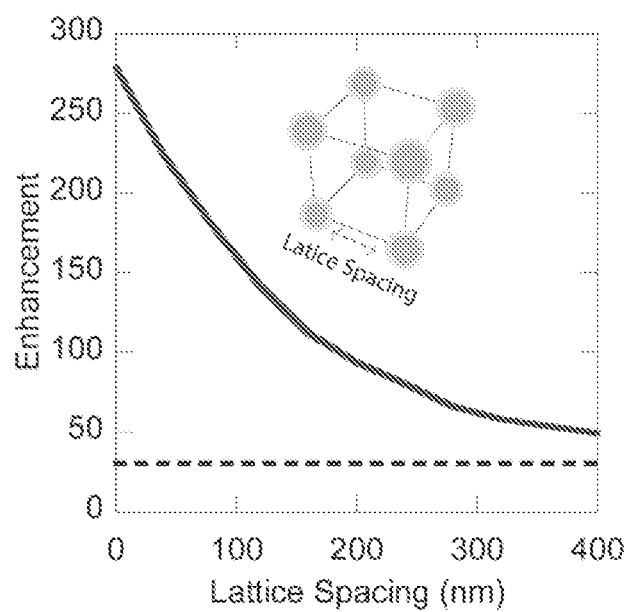
FIG. 6 illustrates matrix effect. The nanoshells are 100 nm in diameter and 30 nm thick. The spacing between them is increased and the enhancement is calculated. X-ray energy is fixed at 40 keV. The solid line shows the total enhancement, which is much higher than the enhancement from a single nanoshell (dashed line).

In reality, it is possible to have a number of nanoshells in water than just a single one, and the enhancement created by this matrix of nanoshells can be much greater than isolated individual shells. FIG. 6 shows enhancement as a function of distance between nanoshells arranged in a matrix: eight nanoshells (50 nm radius and 30 nm thick) are arranged at the corners of a cube. A periodic repeating boundary condition using these nanoshells as the unit cell is adopted here. The highest enhancement is 5 times greater than the isolated individual nanoshells with all the nanoshells touching each other. The cause for this additional enhancement is attributed to neighboring nanoshells, which can be quite significant. The enhancement decreases as the distance between the nanoshells increases. The results show that well-designed nanoassemblies are much more effective in creating local energy deposition than a single large mass sphere shown in FIG. 1 and FIG. 5. A practical example of matrix effect may be found in the aggregated nanoparticles that can generate much higher local/nanoscale enhancements than individual nanoparticles separated by long distances.

Practical Cases

We calculated the enhancement of several possible structures that can be made practically. Although it is possible to make nanoshells with continuous solid walls, making a shell decorated with nanoparticles is more practical. FIG. 7 shows the calculated results of these nanoparticle assemblies. The total amount of gold is the same for all these structures, which is the same as that of the nanoshell. As shown in FIG. 7 the enhancement of a nanoparticle-decorated shell is only slightly less, 25% in this case, than that of a continuous nanoshell of the same mass. As the size of nanoparticles increases, gaps between these larger gold nanoparticles also increase, resulting in the decrease in the solid angle subtended by all the gold nanoparticles toward the VOI inside the nanoshell. Such a decrease leads to smaller enhancements. We also evaluated solid and nanoparticle-decorated parallel double plates, and found that the two enhancements are similar. However, both are lower than that of the nanoshell and the nanoparticle-decorated nanoshells.

Discussion

The geometry enhancement is clearly dependent on irradiation energy, as shown in almost all the results presented in this work using X-rays. There is an optimal X-ray energy at which the highest enhancement can be reached for a given geometry. For example, X-rays slightly above 80 keV should be used to achieve the maximum enhancement for a gold nanoshell. When several elements are present, multiple energies of X-rays may be employed to achieve the highest enhancement.

Because the enhancement is the ratio of energy deposition by the introduced nanomaterials within the VOI to that by the background water, it is critical to correctly calculate the latter as well. If only water in the VOI is used to calculate the X-ray energy absorption and electron energy deposition by the background water, then the enhancement will be incorrectly overestimated. Because we use a macroscopic method to estimate the energy deposition in VOI by electrons generated from water under X-ray irradiation, the enhancement predicted here should be similar to what is measured practically.

One may wonder what happens if two or more effects described above are combined. For example, would the enhancement follow a linear additive relationship if the matrix and composition effects are combined? The answer is almost, but not exactly. The outcome of the combined effect may deviate from the linear sum of the two separate effects because of attenuation of the kinetic energy of the electrons emitted from nanomaterials of different shapes and compositions.

The results shown here suggest that it is possible to achieve a very high physical energy deposition enhancement near the center of just one or a few nanoshells or other shapes, which is based on T2PE. A similar enhancement over the bulk volume based on T1PE may be possible to achieve if much greater amounts of nanomaterials is used. The current discussion focuses on pure PE, i.e., the enhancement originate solely from the enhanced energy deposition over the background water. Besides these two types (T1PE and T2PE), chemical enhancement may occur under certain situations with certain nanostructures.[10] In the future, it is possible to combine PE with chemical and other enhancement mechanisms.

The geometric enhancement investigation discussed here may help detect electrons released from nanoparticles in solution due to the large number of electrons in a small volume. For example, it is possible to develop nanoparticle-decorated nanoshells as shown in FIG. 7 with optical fluorophores or scintillators trapped inside for detection of these electrons via in situ optical microscopy by probing the fluorescence through electron excitation or ionization. More advanced synthetic and detection methods may be needed to experimentally investigate the mechanisms of energy deposition and transfer. For example, it is possible to use fluorescent core-shell nanostructures to detect fluorescence from the fluorescent semiconductor shell excited by the electrons released from the gold core.[11]

Based on these calculations, it is clear that nanoshells of carefully chosen dimensions can create high energy deposition densities near the center of these nanoshells. As shown in FIG. 7, the shells are not required to be continuous or completely solid. A shell decorated with a layer of large nanoparticles can reach nearly the same enhancement at the center of such a porous shell. For example, it is shown that small gold nanoparticles can be linked to or embedded in the surface of lipid shells.[12] Although these nanoparticles are too small to influence energy deposition as discussed here, it is possible to connect larger gold nanoparticles to the shell. This not only makes the synthesis easier but also facilitates the release of the content in the nanoshell delivered to a target. Other synthetic possibilities exist. For instance, there are a number of reports on how to make nanostructures such as nanoshells, nanocages, nanotubes and nanocylinders that may be adopted to studying the enhancement described here.[13-15] These synthetic studies may pave the way for realizing the enhancement described here. The shaped nanostructures described here may be suitable for capturing other energetic particles such as gamma rays, positrons, neutrons and electrons, and converting them into local energy deposition.

Geometric Optimization of Nanoeggs

Nanoshells are compared with a similar nanostructure, nanoeggs. The yolk, which is a sphere at the center of the shell, and the shell of nanoeggs are both made of gold. FIG. 11A and FIG. 11B show two-dimensional contour plots of energy deposition in nanoshells and nanoeggs. Both types of nanostructures contain 8 mass units and the X-ray energy is set at 81 keV. The enhancement is computed as the energy deposited in the VOI of 1-nm thick shells of water at a varying distance away from the center (horizontal-axis in FIG. 11A/11B). The radii of the nanoshells are changed while the amount of gold is fixed (FIG. 11A). In the nanoegg case, the yolk is fixed at 25 nm in radius or 10% of the total mass (FIG. 11B). The enhancement is computed for different shell thicknesses. The highest enhancement occurs near the center for nanoshells or the yolk for nanoeggs, suggesting that the overlap of electrons going through the inner space leads to the increased enhancement inside. There is a significant decrease of enhancement right outside the wall of the shell, mainly caused by the decreased total solid angle subtended by the total amount of Au in both shapes as the VOI moves from inside to outside. As can be seen in FIG. 11A and FIG. 11B, nanoeggs in these cases generate smaller enhancements than nanoshells of equal mass. FIG. 11C and FIG. 11D show similar results for nanoshells and nanoeggs at two specific radii of 30 and 70 nm with 30- and 11-nm shell thickness. For these two shapes, the maximum enhancements are close, which are ~23 times.

FIG. 12A depicts the enhancement both as a function of the percentage of the mass in the yolk and total mass in nanoeggs. Total mass is varied from 4 to 32 mass units, and yolk changes from 0% (i.e., a nanoshell) to 100% (i.e., a solid sphere). The X-ray energy is set at 40 keV. It shows that at a fixed mass, the enhancement decreases from the nanoshell to nanoegg and then to nanosphere. We further explored the contribution of different sub-shells in a nanoshell to the overall enhancement. FIG. 12B reveals the enhancement as a function of mass or volume of the shells. In this calculation, the total mass of the nanoshell has 32 mass units. The enhancement from the innermost layer or shell of 4-mass units alone is almost 50% of the total enhancement offered by the 32-unit mass shell. Adding another 4-mass unit shell increases the enhancement by less than 20%, even though the mass is doubled. After adding another 8 units of mass, the enhancement increases further, but again much less than doubling for the 16-mass unit shell. Finally, the last layer of 16 units of mass is added to form the 32-mass unit nanoshell, and the results show that the 28 mass units added to the 4-mass unit nanoshell only doubles the enhancement. These results show that the innermost layer of gold is the most important. Although each addition of gold layer further increases the enhancement, the amount of enhancement decreases from 6.25× per unit mass for a 4-unit mass nanoshell to 1.56× per unit mass for a 32-unit mass shell. The exact trend depends on the X-ray energy, material, and shape, but the contribution per unit mass generally decrease as the total mass increases. These results suggest that a balance between the total amount of gold and the absolute enhancement should be considered when designing these nanostructures.

Composition Optimization

With regard to composition, it is found that adding a second element to the mix may change enhancement. For example, when Au is partially replaced by Pt in a Au nanoshell, enhancement may increase slightly, depending on the exact geometric configuration and X-ray energy. FIG. 13 shows the results of replacing an outside layer of Au in a gold nanoshell with a Pt layer, each containing 4 mass units. The results show that such a change may increase the enhancement if the X-ray energy is correctly selected. For instance, the enhancement increases from 45 to 50 times when the X-ray energy is set to ~85 keV. This is because electrons emitted from the outer layer of the nanoshell need to penetrate the inner layer to reach the VOI at the center and deposit energy there. If the photoelectrons originated from the outer layer possess a slightly greater kinetic energy, then the enhancement can be increased. Because the absorption edge of Pt is 2 keV lower than that of Au, Pt emits electrons with 2-keV greater kinetic energy than Au after absorbing the same X-rays. As a result, the peak electron kinetic energy is up-shifted by 2 keV for the electrons generated from the Pt outer layer to penetrate the inner gold layer. If the inner layer is thicker, then lighter elements may be used to increase the enhancement. Further optimization may be possible, by selecting materials and energy of X-rays.

Example 2: Liposomes Coated with Gold Nanoparticles

This Example demonstrates the formation of polymerizable liposomes and their cargo-carrying capacity. This Example further demonstrates that polymerizable liposomes can be coated in gold nanoparticles for use in geometry enhancement of cargo release from the liposomes.

Materials and Methods

Liposome Preparation.

Liposomes were produced through the standard extrusion method of making liposomes. A combination of membrane filters from 100 to 600 nm was used in the extrusion method. Three kinds of lipid molecules were used to construct the gold nanoparticle-coated X-ray polymerizable liposomes, as illustrated in FIG. 15E. Three types of lipids form the liposomes: DPPC, DPPE, and Bis-SorbPC. DPPC are regular lipid molecules. DPPE has amine groups that can attract citrate-covered gold nanoparticles. Bis-Sorb-PC polymerize under X-ray irradiation, which renders the liposome open to release cargos inside.

Results

Figure 15:
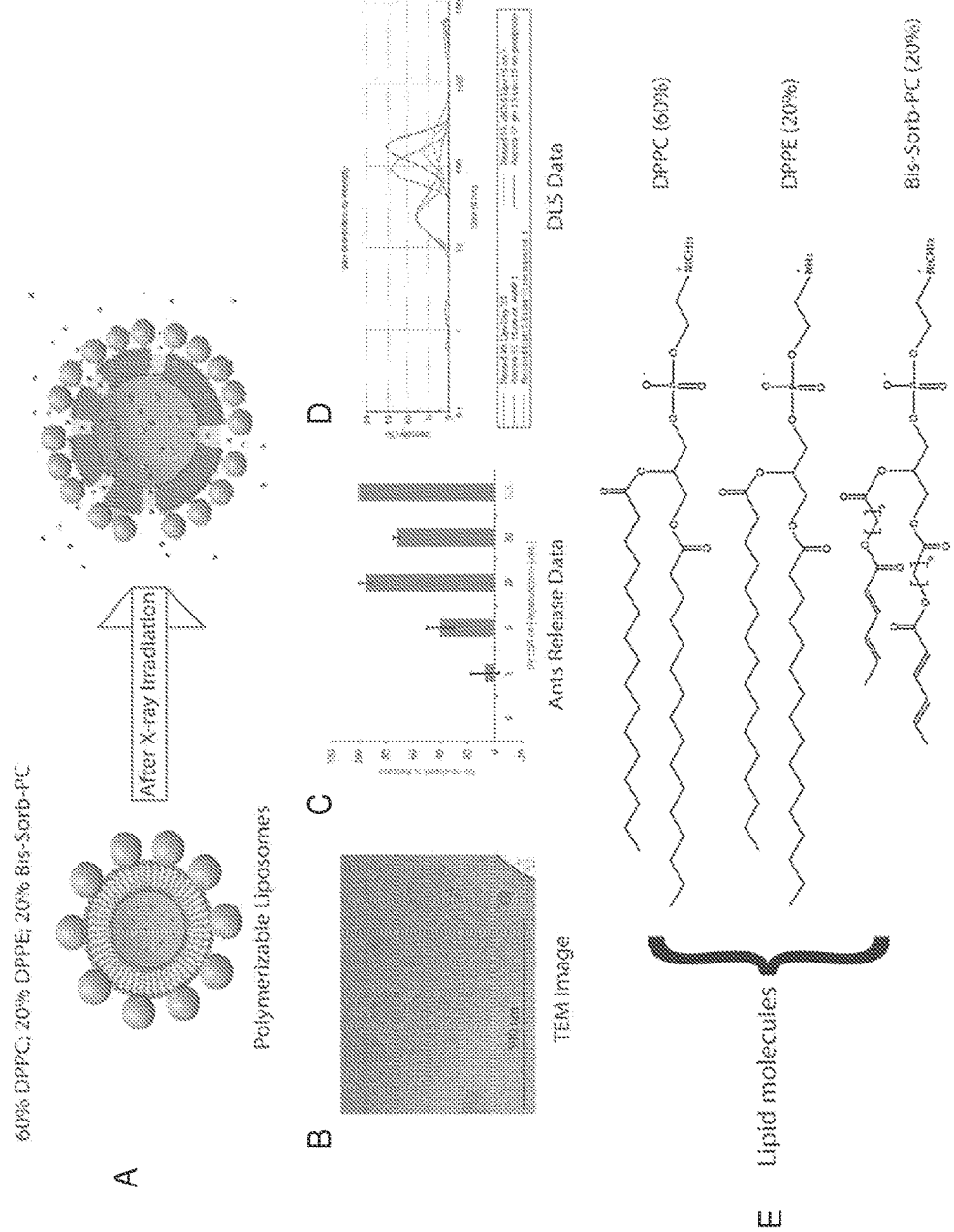
FIG. 15 illustrates gold nanoparticle-coated polymerizable liposomes as cargo delivery systems.

Liposomes coated with gold nanoparticles with cargo inside are shown in FIG. 15A. Overall, FIG. 15 illustrates how an exemplary gold nanoparticle is made so that they can be used in X-ray triggered cargo release applications. FIG. 15A shows the proposed mechanism of cargo release. Without wishing to be bound by theory, it is believed that T2PE created by the shell of gold nanoparticles generate OH radicals inside the liposome. These radicals then react with the polymerizable lipid molecules Bis-SorbPC to cause them to polymerize. This polymerization then leads to the openings of the liposomes and the release of the drug molecules inside.

Liposomes were prepared (See Materials and Methods) and analyzed using cryo transmission electron microscopy. The resulting liposomes are illustrated in FIG. 15B.

Figure 16:
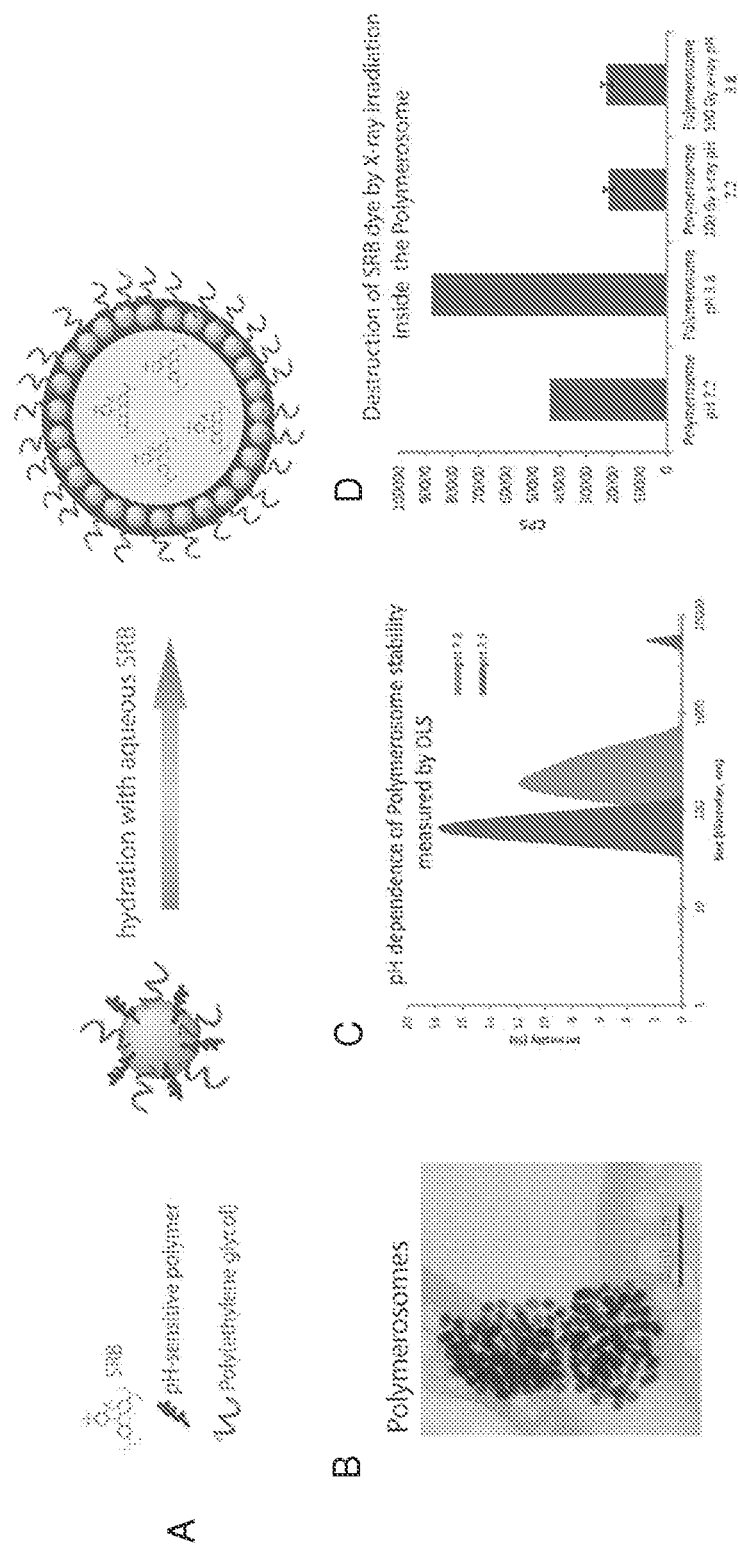
FIG. 16 illustrates polymersomes made from gold nanoparticles functionalized with amphillic ligands.

To demonstrate irradiation-triggered release of cargo from the liposomes, the compound 8-aminonaphthalene-1,3,6-trisulfonic acid (ANTS) and its quencher p-xylene-bis-pyridinium bromide (DPX) were mixed with UV polymerizable lipid molecules (DC(8,9)PC) to form cargo-carrying liposomes. After liposomes were formed, the solution was purified via centrifugation to remove free ANTS/DPX. The liposomes are then exposed to UV light to cause DC(8,9)PC to polymerize and release ANTS/DPX from the liposomes. FIG. 15C shows the release of the cargo content (ANTS) from inside the liposomes upon breaking the liposomes with UV radiation (254 nm). Once released and diluted, ANTS fluoresce more intensely, which was measured with fluorometry. FIG. 16C shows increased fluorescence for longer UV irradiation.

Liposomes were further incubated with gold nanoparticles. FIG. 16D shows dynamic light scattering data from three samples: the gold nanoparticles, the DPPE/DPPC liposomes, and the mixture of the two. It shows that the mixture has a larger diameter by twice the diameter of the gold nanoparticles, suggesting the coating of gold nanoparticles. Similar results were found in gold nanoparticle-coated silica nanoparticles, which was subsequently confirmed via transmission electron microscope. The formed liposomes coated in gold nanoparticles may generate large T2PE. For 15 nanoparticles used here, the enhancement may be 2-5 times higher. Larger gold nanoparticles and smaller sized liposomes will possess higher enhancement.

Example 3: Polymersomes Made with Gold Nanoparticles

This Example demonstrates the construction of polymersomes formed with gold nanoparticles. The polymersomes formed with gold nanoparticles exhibit enhanced release of cargo from the polymersome upon X-ray irradiation.

Materials and Methods

Construction of Polymersomes Coated with Gold Nanoparticles.

Polymersomes were formed by mixing amphiphillic nanoparticles in water. A shell of gold nanoparticles embedded in a shell of polymers was formed.

Results

As shown in FIG. 16A and FIG. 16B, polymersomes formed from 15-nm gold nanoparticles coated with the amphiphillic ligands of polyethylene glycol (PEG) and poly methyl methacrylate and vinylpyridine (PMMAVP). Polymersomes formed with gold nanoparticles were incubated with the dye molecule sulforhodamine B (SRB). These polymersome illustrate an example of a shell of gold nanoparticles embedded in a shell of polymers. This is shown in FIG. 16A. FIG. 16B shows a transmission electron microscope image of two such polymersomes.

The gold nanoparticle-containing polymersomes carrying the SRB dye cargo in the center were exposed to pH adjustment. The pH of the solution housing these polymersomes was changed from 7.2 to 3.5. As can be seen in FIG. 16C, the polymersomes are pH-sensitive and changing the pH from 7.2 to 3.5 resulted in an increase in the release of the SRB from the center of the gold nanoparticle-containing polymersome carrying the SRB dye.

The gold nanoparticle-containing polymersomes carrying the SRB dye cargo were exposed to X-ray irradiation (FIG. 16D). Fluorescence was decreased in both pH 7.2 and pH 3.8 in response to 100 Gy of X-ray irradiation. Fluorescence of SRB molecules is known to be reduced under X-ray irradiation. These results suggest the use of X-ray irradiation may be an effective means at enhancing the cargo-releasing capabilities gold nanoparticle-containing polymersomes.

REFERENCES

1. Foley, E.; Carter, J.; Shan, F.; Guo, T., Chemical Communications 2005, (25), 3192-3194.
2. Hainfeld, J.; Slatkin, D.; Smilowitz, H., Physics in Medicine and Biology 2004, 49, (18), N309-N315.
3. Renault, J. P.; Musat, R.; Moreau, S.; Poidevin, F.; Mathon, M. H.; Pommeret, S., Physical Chemistry Chemical Physics 2010, 12, (39), 12868-12874.
4. Carter, J. D.; Cheng, N. N.; Qu, Y. Q.; Suarez, G. D.; Guo, T., Journal of Physical Chemistry B 2007, 111, (40), 11622-11625.
5. Cho, S. H.; Jones, B. L.; Krishnan, S., Physics in Medicine and Biology 2009, 54, (16), 4889-4905.
6. Cho, S. H.; Jones, B. L.; Krishnan, S., Medical Physics 2010, 37, (7), 3809-3816.
7. Pradhan, A. K.; Nahar, S. N.; Montenegro, M.; Yu, Y.; Zhang, H. L.; Sur, C.; Mrozik, M.; Pitzer, R. M., Journal of Physical Chemistry A 2009, 113, (45), 12356-12363.
8. Van den Heuvel, F.; Locquet, J. P.; Nuyts, S., Physics in Medicine and Biology 2010, 55, (16), 4509-4520.
9. Kobayashi, K.; Usami, N.; Porcel, E.; Lacombe, S.; Le Sech, C., Mutation Research-Reviews in Mutation Research 2010, 704, (1-3), 123-131.
10. Cheng, N. N.; Starkewolf, Z.; Davidson, A. R.; Sharmah, A.; Lee, C.; Lien, J.; Guo, T., JACS 2012, ASAP, (January 19).
11. Klimov, V. I.; Liu, N. G.; Prall, B. S., Journal of the American Chemical Society 2006, 128, (48), 15362-15363.
12. Chithrani, D. B.; Dunne, M.; Stewart, J.; Allen, C.; Jaffray, D. A., Nanomedicine-Nanotechnology Biology and Medicine 2010, 6, (1), 161-169.
13. Hu, M.; Petrova, H.; Chen, J. Y.; McLellan, J. M.; Siekkinen, A. R.; Marquez, M.; Li, X. D.; Xia, Y. N.; Hartland, G. V., Journal of Physical Chemistry B 2006, 110, (4), 1520-1524.
14. Pham, T.; Jackson, J.; Halas, N.; Lee, T., Langmuir 2002, 18, (12), 4915-4920.
15. Qu, Y. Q.; Porter, R.; Shan, F.; Carter, J. D.; Guo, T., Langmuir 2006, 22, (14), 6367-6374.
16. Hubbell, J. H.; Seltzer, S. M., Tables of X-Ray Mass Attenuation Coefficients and Mass Energy-Absorption Coefficients. In NIST.
17. http://geant4.cern.ch/
18. Joy, D.; Luo, S., Scanning 1989, 11, (4), 176-180.
19. Semenenko, V. A.; Turner, J. E.; Borak, T. B., Radiation and Environmental Biophysics 2003, 42, (3), 213-217.
20. Song, J. B., J. J. Zhou, and H. W. Duan. Journal of the American Chemical Society, 2012. 134(32): p. 13458-13469.
21. Ma, N., et al. Journal of the American Chemical Society, 2010. 132(2): p. 442-+.
22. Guo, R., et al. Journal of Materials Chemistry, 2011. 21(13): p. 5120-5127.

What is claimed:

1. A method of enhancing deposition of ionizing radiation energy in a solution, comprising:
    A) providing a nanoshell comprising metal atoms, wherein the nanoshell has scaffolding molecules with nanoparticles on the scaffolding molecules, wherein the metal atoms are in the nanoparticles, wherein the scaffolding molecules comprise a lipid bilayer characterized by a radius of between about 1 nm and about 1000 nm, and wherein the spacing between nanoparticles on the scaffolding molecules is between about 1 nm and 500 nm;
    B) subjecting the nanoshell to ionizing radiation, wherein electrons are released from the metal atoms of the nanoshell and deposition of energy from the ionizing radiation is enhanced in the solution adjacent to the nanoshell.

2. The method of claim 1, wherein the metal atoms are from a heavy metal.

3. The method of claim 2, wherein the heavy metal is selected from the group consisting of gold, platinum, bismuth, uranium, and tungsten.

4. The method of claim 1, wherein the metal atoms are selected from the group consisting of iron, zinc, and silver.

5. The method of claim 1, wherein the nanoshell further comprises at least one of silicon and oxygen.

6. The method of claim 1, wherein the nanoshell is continuous.

7. The method of claim 1, wherein the nanoshell comprises a shell of nanoparticles.

8. The method of claim 7, wherein the shell of nanoparticles comprises gold nanoparticles.

9. The method of claim 8, wherein the shell of nanoparticles comprises a combination of gold nanoparticles and platinum nanoparticles.

10. The method of claim 1, wherein the ionizing radiation is X-rays.

11. The method of claim 1, wherein the enhancement is a 60-fold increase in the deposition of energy from the ionizing radiation in the solution adjacent to the nanoshell when compared to the deposition of energy from the ionizing radiation in the background solution.

12. The method of claim 1, wherein the lipid bilayer comprises a combination of lipids including Bis-Sorb-PC, and wherein the ratio of Bis-Sorb-PC to other lipids is between about 1%:99% and about 30%:70%.

13. The method of claim 1, wherein the deposition of energy from the ionizing radiation in the solution adjacent to the nanoshell occurs at a distance of at least 5 nm.

14. The method of claim 1, wherein the nanoshell further comprises nitrobenzene, a monomer, an optical fluorophore, or a cancer probe.

15. The method of claim 1, wherein the deposition of energy from the ionizing radiation is enhanced to a greater degree within the nanoshell than external to the nanoshell.

16. A method of enhancing deposition of ionizing radiation energy in a solution, comprising:
   A) contacting a nanoshell comprising metal atoms with ionizing radiation, wherein the nanoshell has scaffolding molecules with nanoparticles on the scaffolding molecules, wherein the metal atoms are in the nanoparticles, and wherein the spacing between nanoparticles on the scaffolding molecules is between about 1 nm and 1000 nm;
   B) releasing electrons from the metal atoms of the nanoshell, wherein deposition of energy from the ionizing radiation is enhanced in the solution adjacent to the nanoshell.

17. The method of claim 16, wherein the metal atoms are from a heavy metal.

18. The method of claim 17, wherein the heavy metal is selected from the group consisting of gold, platinum, bismuth, uranium, and tungsten.

19. The method of claim 16, wherein the metal atoms are selected from the group consisting of iron, zinc, and silver.

20. The method of claim 16, wherein the nanoshell further comprises at least one of silicon and oxygen.

21. The method of claim 16, wherein the nanoshell is continuous.

22. The method of claim 16, wherein the nanoshell comprises a shell of nanoparticles.

23. The method of claim 22, wherein the shell of nanoparticles comprises gold nanoparticles.

24. The method of claim 16, wherein the nanoshell further comprises a lipid.

25. The method of claim 16, wherein the ionizing radiation is rays.

26. The method of claim 16, wherein the enhancement is a 60-fold increase in the deposition of energy from the ionizing radiation in the solution adjacent to the nanoshell when compared to the deposition of energy from the ionizing radiation in the background solution.

* * * * *

UNITED STATES PATENT AND TRADEMARK OFFICE
CERTIFICATE OF CORRECTION

PATENT NO. : 9,764,305 B2
APPLICATION NO. : 14/391003
DATED : September 19, 2017
INVENTOR(S) : Ting Guo It is certified that error appears in the above-identified patent and that said Letters Patent is hereby corrected as shown below:

In Column 20, Lines 23-24, Claim 25, "the ionizing radiation is rays" should read -- the ionizing radiation is X-rays --

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*